United States Patent
Young et al.

[11] 4,361,473
[45] Nov. 30, 1982

[54] POTASSIUM ION-SELECTIVE MEMBRANE ELECTRODE

[75] Inventors: Chung C. Young, Natick; John P. Willis, Sudbury, both of Mass.

[73] Assignee: Nova Biomedical Corporation, Newton, Mass.

[21] Appl. No.: 315,919

[22] Filed: Oct. 28, 1981

[51] Int. Cl.$^3$ .............................................. G01N 27/30
[52] U.S. Cl. ................................ 204/195 M; 549/347
[58] Field of Search ......................... 204/195 M, 1 A; 128/635; 549/347

[56] References Cited

U.S. PATENT DOCUMENTS 4,233,136  11/1980  Spaziani et al. ................. 204/195 L

OTHER PUBLICATIONS

Toshiyuki Shono et al., J. Electroanal. Chem., 132, 99–105, (1982).
E. Pretsch et al., Research/Development Magazine, vol. 25, No. 3, pp. 20–23, Mar. 1974.
Tamura et al. (1980), Bull. Chem. Soc. Jpn., 53, 547–548.
Kimura et al. (1979), J. Electroanalyt. Chem. 95, 91–101.
Cammann (1979), Working with Ion-Selective Electrodes, Chemical Laboratory Practice, 80.
Pederson (1967), J. Amer. Chem. Soc. 89:26, 7020–7036.

Primary Examiner—G. L. Kaplan

[57] ABSTRACT

In an electrode for determining the potassium ion content of a liquid sample to be tested, the electrode including a membrane having incorporated therein an ion selective component, the improvement in which the ion specific component is a compound of the formula:

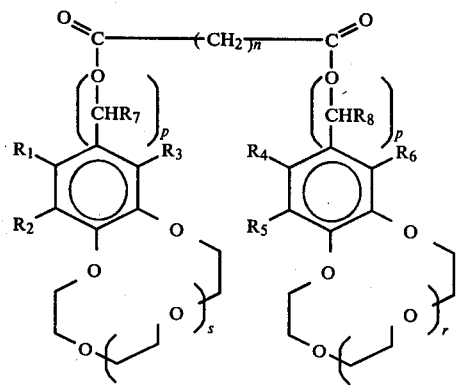

wherein each $R_1$, $R_2$, $R_3$, $R_4$, $R_5$, $R_6$, $R_7$, and $R_8$ is hydrogen or an alkyl group containing between one and about 20 carbon atoms, p is 0 or 1, n is one or more, and, each s and r, independently, is 1, 2, or 3, provided that, when p is 1, n is 8 or more.

14 Claims, 1 Drawing Figure

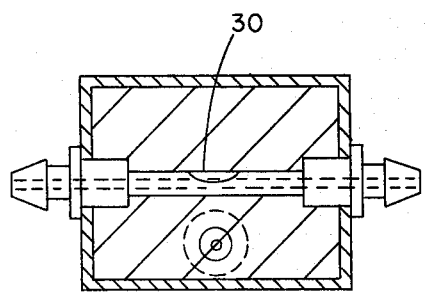

POTASSIUM ION-SELECTIVE MEMBRANE ELECTRODE

This invention relates to electrodes for determining the potassium ion content of a liquid sample.

Such electrodes commonly contain a membrane incorporating an ion specific component. A number of substances have been employed as ion specific components, including e.g., antibiotics such as valinomycin. More recently there has been described, in Kimura et al. (1979) J. Electroanalyt. Chem. 95, 91–101, an electrode membrane containing one of a group of bis and poly crown ethers. Four of the bis crown ethers used had the following formula:

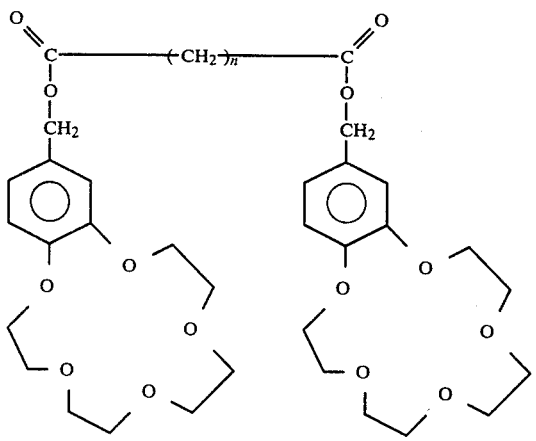

(1)

where n = 1, 3, 5 or 7. Each crown ether, together with dibutyl phthalate and polyvinyl chloride (PVC), was dissolved in tetrahydrofuran. The Kimura Kamuri et al. paper states, p. 97: "(T)he bis (crown ether)s having too long or too short a chain [separating the rings] have difficulty in achieving a high degree of interaction between the two adjacent crown ether rings and an ion, and the appropriate length of the chain connecting two crown ether rings is, therefore, necessary to form stable 2:1 complex. The selectivity for sodium estimated here may suggest that bis (crown ether) (n=5) forms most stable 2:1 complex among these bis (crown ether)s."

In general, the present invention features an improvement in an electrode for determining the potassium ion content of a liquid sample to be tested. The improvement is the presence, in the membrane of such an electrode, as the ion specific component thereof, of a compound of the formula:

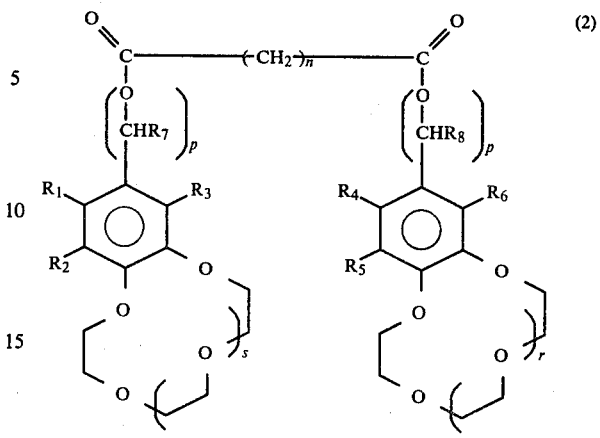

(2)

wherein each $R_1$, $R_2$, $R_3$, $R_4$, $R_5$, $R_6$, $R_7$, and $R_8$ is hydrogen or an alkyl group containing from one to twenty carbon atoms, preferably from one to five carbon atoms, p is 0 or 1, each s and r, independently, is 1, 2 or 3, and n is one or more, provided that, when p is 1, n is eight or more.

In particular embodiments, "n" in the general formula is no greater than 14, s and r are 2, and p is 1; the preferred compound of this formula is bis-(4'-methylbenzo-15-crown-5) dodecanedioate. Preferably the membrane further contains a plastic material and a nonvolatile plasticizer, which is preferably dibenzyl pimelate. The membrane preferably also contains an anion excluder, most preferably a tetraphenylborate salt (TPB), and an ion transport enhancer, most preferably a dipicrylamine salt (DPA).

The electrode containing the membrane of the invention provides accurate measurements of the potassium ion content of liquids, particularly blood and urine. The membrane also advantageously exhibits long life. Furthermore, perhaps most importantly, the membrane's drift stability is very good; i.e., the difference between the measured electrical potential of a standard before and after an analysis is very low, so that drift-related measurement errors are minimized.

Other objects, features and advantages of this invention will be apparent to those skilled in the art from the following detailed description of a preferred embodiment thereof, taken together with the accompanying drawing, in which:

The FIGURE is a sectional view of an electrode assembly embodying the invention.

The electrode assembly shown in the FIGURE is as shown and described in Spaziani et al. U.S. Pat. No. 4,233,136, hereby incorporated by reference.

In the preferred embodiment of the present invention, membrane 30 comprises an organic plastic matrix, polyvinylchloride, containing the ion selective compound bis-(4'-methylbenzo-15-crown-5) dodecanedioate, of the formula:

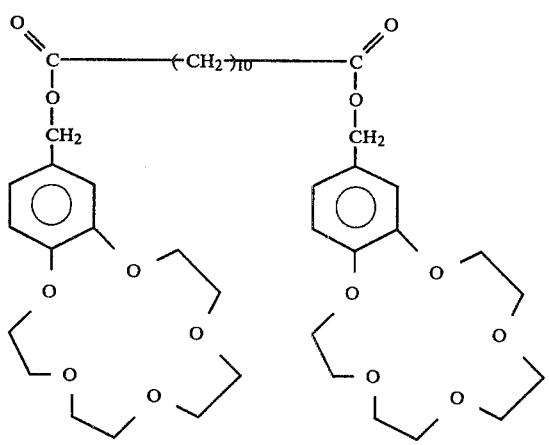
(3)

The ion selective compound is dissolved in the plasticizer dibenzyl pimelate, which also contains TPB and DPA. The membrane materials are all soluble in the volatile solvent tetrahydrofuran.

The amount of PVC, which provides support for the membrane, is controlled to provide support without interfering with the electrochemical properties of the membrane. The membrane comprises 8 to 30% PVC, by weight, preferably 12 to 20%, and is greater than 1 mil, preferably 8 to 12 mils, thick.

The first step in preparing the ion specific compound bis-(4'-methylbenzo-15-crown-5)-dodecanedioate is to prepare 4'-formylbenzo-15-crown-5, according to the procedure described in Ungaro et al. (1976) J. Am. Chem. Soc. 98, 5198, as follows.

A solution of 59.4 g (0.43 moles) of 3, 4-dihydroxybenzaldehyde (Tridom Fluka Inc., Hauppaque, N.Y., Cat. No. 37520) dissolved in 2 liters of nitrogen-purged n-butanol is charged with 34.4 g (0.86 moles) of NaOH dissolved in 25 ml of water, heated to reflux and, with stirring, 99.4 g (0.43 moles) of bis(2-(2-chloroethoxy) ethyl ether (Parish Chemical Co., Orem. Ut., Cat. No. 1401) is then added dropwise over a period of 10 to 15 min. After 24–36 hrs. of reflux the mixture is cooled to room temperature, acidified with 6 N HCl, filtered, the solids washed with methanol, and the combined filtrates evaporated, using a Buchi-Brinkman rotary evaporator, until no n-butanol can be detected. The residue is dissolved in 300 ml of methylene chloride and washed in turn with 150 ml water (3 times), 150 ml 5% $K_2CO_3$ (3 times), dried over anhydrous sodium sulfate, and evaporated to dryness. The oily dark brown residue is then continuously extracted with hot heptane, which upon cooling yields white crystals.

Recrystallization from 4:1 heptane-toluene yields 4'-formylbenzo-15-crown-5. This product is then reduced with sodium borohydride in ethanol, as described in Kimura et al., Id., to yield 4'-hydroxymethylbenzo-15-crown-5, one of the reagents needed to make the compound of formula (3).

Another reagent, dodecanedioyl chloride, is obtained by the reaction of thionyl chloride with dodecanedioic acid ($C_{12}H_{22}O_4$, Aldrich Chemical Co., Milwaukee, WI, Cat. No. D100-9) according to the procedure described in J. Org. Chem., 28, 1495 (1958).

Bis-(4'-methylbenzo-15-crown-5)-dodecanedioate is obtained by the reaction of two moles of 4'-hydroxy methylbenzo-15-crown-5 with one mole of dodecanedioyl chloride and two moles of triethylamine in methylene chloride according to the procedure of Kimura et al., Id.

The plasticizer dibenzyl pimelate, of the formula

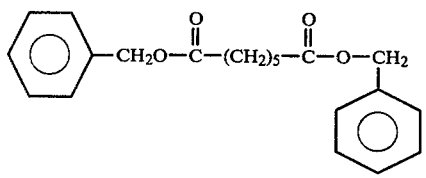

is prepared by reacting two moles of benzyl alcohol with one mole of pimeloyl chloride in methylene chloride with refluxing.

To make the membrane, 0.24 g of high molecular weight polyvinylchloride polymer in powder form, having a density of 1.40 grams/cc. (Aldrich Chemical Company of Milwaukee, Wisconsin, Catalog No. 18956-1), is dissolved in 5 ml tetrahydrofuran. To this solution are then added 1.00 g of non-volatile solvent plasticizer dibenzyl pimelate together with 50 mg of the ion selective compound bis-(4'-methyl benzo-15-crown-5) tetradecanedioate. Also added, in mole ratios to the ion selective compound of, respectively, 0.1:1 and 4:1, is the potassium salt of DPA, and the potassium salt of TPB. TPB is added because it contains a large anion and is thus known to prevent smaller anions such as $Cl^-$ from creating an interference. In the instant case it was found that, unexpectedly, it caused an improved response slope as well. The DPA was found to enhance membrane transport properties, and also provided the unexpected benefit of enhanced stability of the electrode potential.

The membrane is made from the solution thus formed, as described in Spaziani et al., Id. Such a membrane demonstrated good mechanical strength and good analytical performance, as shown in line 10 of Table I below. The slope was near Nernstian, 58.0 mv, and drift in both serum and an aqueous solution was very slight. The selectivity coefficient, potassium over sodium, was $1.6 \times 10^{-3}$.

TABLE I

| Membrane | $R_1R_8$ | p | s | r | n | Ion selective Compound % (by weight) | Plasticizer % (by weight) | PVC % (by weight) | Mole Ratio TPB to Ion Selective Compound | Mole Ratio DPA to Ion Selective Compound | Slope (mv) | Standard A Drift Range (mv) Aqueous | Serum |
|---|---|---|---|---|---|---|---|---|---|---|---|---|---|
| 1 | H | 1 | 2 | 2 | 8 | 4.0 | 80.0 | 16.0 | 0.0 | 0.0 | 56.0 | −1 to −4 | −3 to −8 |
| 2 | H | 1 | 2 | 2 | 8 | 3.6 | 72.6 | 14.5 | 4:1 | 0.0 | 57.0 | −0.5 to −3 | −2 to −6 |
| 3 | H | 1 | 2 | 2 | 8 | 4.0 | 79.2 | 15.8 | 0.0 | 0.25:1 | 57.6 | −0.1 to −3 | −1 to −7 |
| 4 | H | 1 | 2 | 2 | 8 | 3.6 | 72.1 | 14.3 | 4:1 | 0.25:1 | 56.4 | +0.1 to −1 | −1 to −2 |
| 5 | H | 1 | 2 | 2 | 9 | 4.0 | 80.1 | 15.9 | 0.0 | 0.0 | 56.1 | −2 to −3 | −4 to −5 |

TABLE I-continued

| Membrane | $R_1R_8$ | p | s | r | n | Ion selective Compound % (by weight) | Plasticizer % (by weight) | PVC % (by weight) | Mole Ratio TPB to Ion Selective Compound | Mole Ratio DPA to Ion Selective Compound | Slope (mv) | Standard A Drift Range (mv) Aqueous | Standard A Drift Range (mv) Serum |
| --- | --- | --- | --- | --- | --- | --- | --- | --- | --- | --- | --- | --- | --- |
| 6 | H | 1 | 2 | 2 | 9 | 4.0 | 72.7 | 14.4 | 4:1 | 0.0 | 56.5 | −1 to −3 | −4 to −5 |
| 7 | H | 1 | 2 | 2 | 9 | 4.0 | 79.3 | 15.8 | 0.0 | 0.25:1 | 56.5 | −1 to −2 | −3 to −4 |
| 8 | H | 1 | 2 | 2 | 9 | 3.6 | 72.0 | 14.4 | 4:1 | 0.25:1 | 56.0 | −0.2 to −2 | −1 to −3 |
| 9 | H | 1 | 2 | 2 | 10 | 4.0 | 80.0 | 16.0 | 0.0 | 0.0 | 58.0 | −0.2 to −3 | −0.6 to −3 |
| 10 | H | 1 | 2 | 2 | 10 | 3.6 | 72.0 | 14.5 | 4:1 | 0.0 | 56.0 | 0 to −2 | 0 to −3 |
| 11 | H | 1 | 2 | 2 | 10 | 4.0 | 79.3 | 15.8 | 0.0 | 0.25:1 | 55.7 | −0.1 to −1 | −0.1 to −2 |
| 12 | H | 1 | 2 | 2 | 10 | 3.6 | 72.0 | 14.4 | 4:1 | 0.25:1 | 55.3 | +0.2 to +0.7 | +0.4 to +0.6 |

The drift for each membrane listed in Table I is determined on the basis of the related concepts of drift and calibration.

In all ion specific electrode measurements the electrodes must be calibrated prior to their use in an analysis. In all cases, at least a two point calibration is performed; in this instance, two internal standards were used. One standard, B, contains 40 mmol/liter $K^+$, while a second, A, contains 4 mmol/liter $K^+$. Prior to an analysis, the potassium electrode is calibrated with these two standards. With each standard, the electrode develops an electrical potential proportional to the logarithm of the concentration of $K^+$. According to the Nernst equation, the logarithm of concentration and potential are linearly related: the difference in potential for a 10 fold change in concentration is 59.1 mv at 25° C. Measurement of potassium in an unknown is performed by comparing the potential developed by the electrode in the sample with the linear calibration graph.

The concept of drift comes in when the electrode potential is again measured, after analysis, against one of the standards (in this case Standard A). The difference between the Standard A potential before and after analysis is drift; the larger the absolute value of this number, the poorer the performance of the electrode in this respect, and the more significant the resultant measurement errors.

An additional measurement, not shown in Table 1, was performed using the membrane and electrode described above. The electrode was used to measure the potassium ion concentration in urine, and gave results in the same accuracy range as those obtained for serum. This was unexpected because urine is known to contain compounds which chemically interfere with valinomycin in a PVC matrix causing, in some instances, extremely inaccurate measurements. For reasons which are as yet unknown, there is apparently no such interference in the case of the membrane described herein, as urine potassium measurements were very accurate.

Other embodiments of the invention are within the following claims. For example, the ion specific substance can be of any configuration within general formula (2). Two such structures, differing from the preferred embodiment only in "n", the length of the chain separating the two rings, produced the analytical results given in lines 1-8 of Table I. Others were prepared in which n was 12 and 14.

The chain length, "n" is varied by preparing the ion selective compound using the appropriate diacid chloride in place of dodecanedioyl chloride in the previously described reaction. For example, if the desired n is 8, the compound is made using sebacoyl chloride, $ClOC(CH_2)_8 COCl$; if n is 9, undecanedioyl chloride, $ClCO(CH_2)_9 COCl$, is used. The chain length "n" is 8 or greater, and preferrably is not greater than 14. The chain length of 8 or greater provides a high molecular weight which advantageously results in increased lipophilicity and hydrophobicity, resulting in good stability (low drift) as well as a decreased tendency to leach out of the membrane, resulting in a longer membrane life.

The ion selective compound can also have side chains in any of the positions indicated by $R_1$-$R_8$ in formula (2). For example, methyl groups can be added to the 4' methyl groups in the two halves of the molecule. As an example, the compound having the formula:

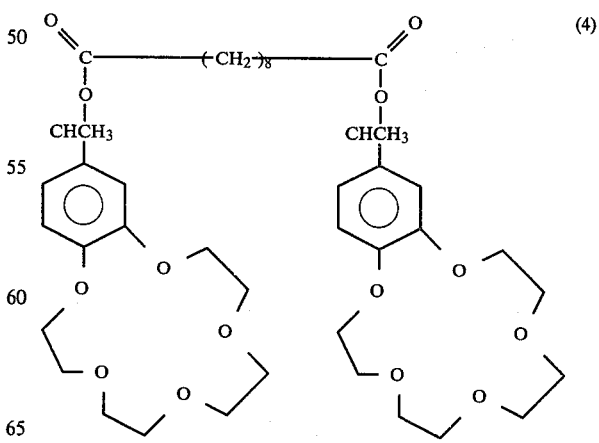

(4)

is prepared according to the reaction sequence shown below.

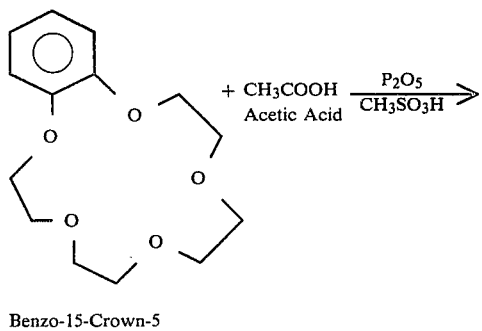

Benzo-15-Crown-5

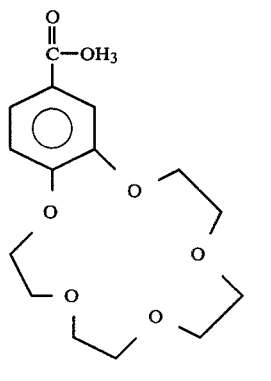

4'-Acetylbenzo-15-Crown-5

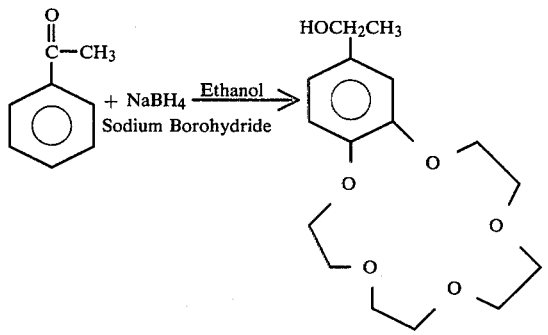

4'-hydroxyethylbenzo-15-Crown-5

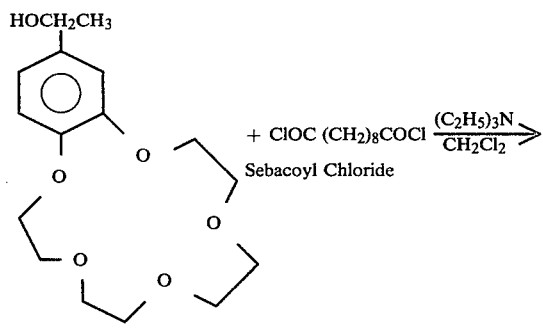

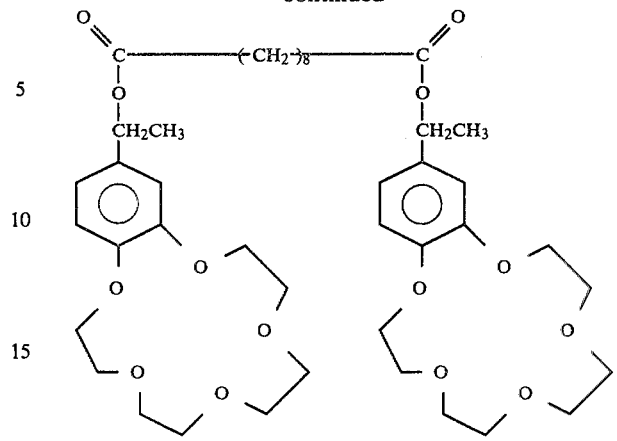

Bis-(4'-ethylbenzo-15-Crown-5) Sebacate

Alkyl side chains, like the long length of the chain between the rings, advantageously serve to increase molecular weight and thereby increase stability and membrane life.

As is indicated in formula (2), the number of oxygen atoms in the rings can range from 4 to 6. For example, the compound

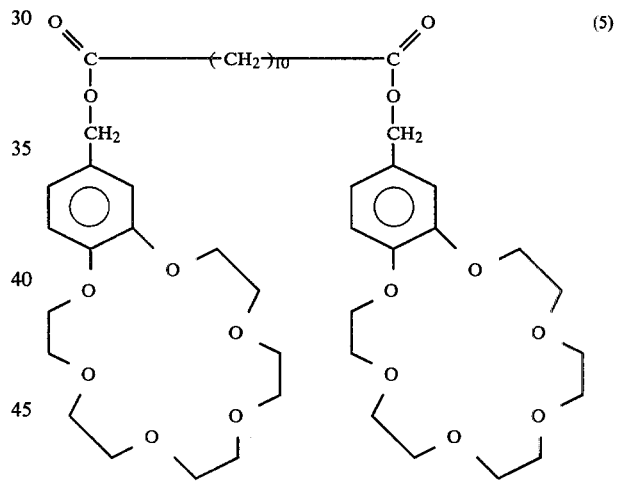

(5)

has six oxygen atoms in each ring. The compound is made according to the procedure described above for making bis-(4' methylbenzo-15-crown-5) dodecanedioate, substituting 1,14-dichloro-3, 6, 9, 12-tetraoxatetradecane (Pedersen (1967) J. Am. Chem. Soc. 89, 7017) for bis (2-(2-chloroethoxy) ethyl) ether.

A membrane prepared using compound (5) exhibited comparatively poor analytical performance, and is thus less preferred than bis- (4' methylbenzo-15-crown-5) dodecanedioate.

The ion specific component can also be a diketone rather than a diester, i.e., "p" in the general formula can be 0 rather than 1. When the compound is a diketone, it is not necessary that n be 8 or greater, because the absence of the two oxygen atoms provides desirable hydrophobicity and therefore improved membrane life. Furthermore, for compounds in which n is low (e.g., below 8), the diketone provides greatly improved drift characteristics compared to the corresponding diester.

Three compounds in which p=0 and n, respectively, equals 5, 10 and 12, were prepared and used in membranes. These compounds are prepared according to the following reaction sequence:

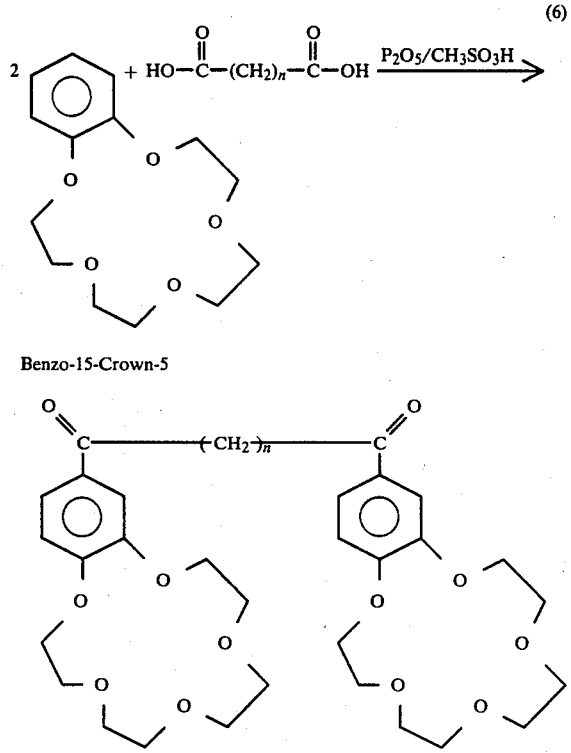

Benzo-15-Crown-5

Using compound (6) in which n=12, a membrane was prepared using the following ingredients.

| | |
|---|---|
| 1.0g | dibenzyl pimelate |
| 0.05g | ion selective compound |
| 0.20g | PVC |
| 0.096g | tetraphenyl borate salt (KTPB) |
| 0.010g | dipicrylamine salt (KDPA) |
| 6ml | tetrahydrofuran |

The membrane exhibited a slope of 56 mv and good analytical performance, including drift in serum of about −1 mv.

Another membrane, prepared using compound (6) in which n=5, contained the following ingredients.

| | |
|---|---|
| 1.0g | dibenzyl pimelate |
| 0.5g | ion selective compound |
| 0.20g | PVC |
| 0.064g | KTPB |
| 0.010g | KDPA |
| 4 ml | tetrahydrofuran |

The properties of this membrane were compared to those of a membrane prepared in an identical manner except that the ion selective compound was bis-(4'-methylbenzo-15 crown-5)-pimelate; i.e., p was 1 and n was 5 in formula (2), and the compound thus was not within the present invention.

In the above comparison, the membrane containing the diketone produced a slope of 56.6 mv and exhibited a Standard A drift in aqueous solution of about 0 mv, and a Standard A drift in serum of about −1 mv. By contrast, the membrane containing the diester, although it produced a similar slope (56.9 mv), exhibited a Standard A drift in aqueous solution of about −8 mv and a Standard A drift in serum of about −20 mv.

Although the non-selective membrane materials described above are preferred, any suitable plastic matrix, non-volatile solvent plasticizer, and volatile solvent can be used. For example, one suitable alternate plasticizer is 2-nitro-p-cymene.

Other plasticizers which can be used, but which work less well, particularly in serum (most give acceptable results in aqueous solutions) include the following: Dibutyl phthalate; Dioctyl adipate; 2-nitro-p-cymene; O-nitrophenyl phenyl ether; Diphenyl ether; Tri(2-Ethyl hexyl) phosphate; Dibenzyl malonate; O-nitrophenyl octyl ether; Di (3-methoxy benzyl) pimelate; Di(3,5-dimethyl benzyl) pimelate; Diethylmethyl malonate; 4-ethyl nitro benzene; nitro benzene; and Escoflex 223 & 250 Dibenzoates (East Coast Chemicals Co., Ceder Grove, N.J.).

Similarly, although TPB, is the preferred anion excluder, other suitable compounds, e.g., picric acid, can be used (caution should be used when handling potentially explosive compounds such as picric acid). And, although an anion excluder improves performance, it is not necessary in situations when less accurate results are acceptable.

Proportions of materials can vary as well. The plastic material generally comprises 8% to 30% of the membrane, by weight. The ion selective compound generally comprises between about 1% and 15% of the membrane, by weight, with about 3–6% being preferred. The plasticizer generally comprises between about 55% and 80% of the membrane by weight, with about 75% being preferred.

If a TPB salt is used, its mole ratio to ion selective compound is between about 0.5:1 and 5:1, with 4:1 being preferred. The mole ratio of DPA to ion selective compound is between about 0.1:1 and 0.3:1, with 0.25 being preferred. These latter two components need not be used in the form of potassium salts, but can be any otherwise non-interfering salt.

What is claimed is:

1. In an electrode for determining the potassium ion content of a liquid sample to be tested, said electrode comprising a membrane having incorporated therein an ion selective component, the improvement wherein said ion specific component comprises a compound of the formula:

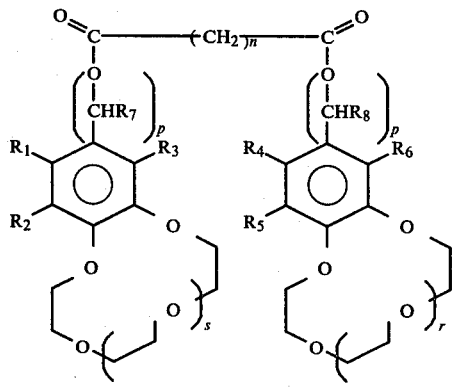

wherein each $R_1$, $R_2$, $R_3$, $R_4$, $R_5$, $R_6$, $R_7$, and $R_8$ is hydrogen or an alkyl group containing between one and about 20 carbon atoms, p is 0 or 1, n is one or more, and, each s and r, independently, is 1, 2, or 3, provided that, when p is 1, n is 8 or more.

2. In the electrode of claim 1, said improvement wherein n is no greater than 14.

3. In the electrode of claim 2, said improvement wherein s is 2 and r is 2.

4. In the electrode of claim 3, said improvement wherein p is 1 and n is at least 8 and no greater than 14.

5. In the electrode of claim 4, said improvement wherein each $R_1$–$R_8$ is hydrogen, each s and r is 2, and n is 8, 9, 10, 12, or 14.

6. In the electrode of claim 5, said improvement wherein said ion selective component is bis-(4-methylbenzo-15-crown-5) dodecanedioate.

7. In the electrode of claim 3, said improvement wherein p is 0.

8. In the electrode of claim 7, said improvement wherein said ion selective component has the formula:

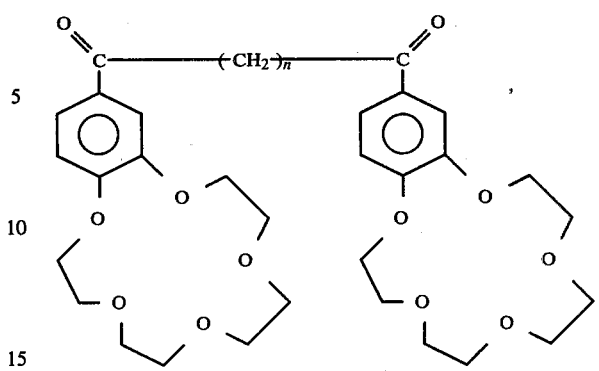

wherein n is 5, 10, or 12.

9. In the electrode of claim 1, said improvement wherein said membrane further comprises a plastic material and a non-volatile solvent plasticizer.

10. In the electrode of claim 9, said improvement wherein said plastic material is polyvinyl chloride and said solvent plasticizer is dibenzyl pimelate.

11. In the electrode of claim 10, said improvement wherein said membrane further comprises a salt of dipicrylamine.

12. In the electrode of claim 11, said improvement wherein said membrane further comprises an anion excluder.

13. In the electrode of claim 12, said improvement wherein said anion excluder is a salt of tetraphenyl borate.

14. In the electrode of claim 13, said improvement wherein said ion selective compound comprises between about 1% and 15% of said membrane, by weight; said plasticizer comprises between about 55% and 80% of said membrane by weight; said polyvinyl chloride comprises between about 10% and 30% of said membrane by weight; said tetraphenyl borate salt is present, in a mole ratio to said ion selective compound, of between 0.5:1 and 5:1; and said dipicrylamine salt is present, in a mole ratio to said ion selective compound, of between 0.1:1 and 0.3:1.

* * * * *

UNITED STATES PATENT AND TRADEMARK OFFICE
CERTIFICATE OF CORRECTION

PATENT NO. : 4,361,473

DATED : November 30, 1982

INVENTOR(S) : Chung Chang Young et al.

It is certified that error appears in the above-identified patent and that said Letters Patent is hereby corrected as shown below:

Column 1, line 45, "Kamuri" should be deleted.

Column 7, second formula from the top, "$OH_3$" should be -- $CH_3$ --.

Signed and Sealed this

Tenth Day of July 1984

[SEAL]

Attest:

GERALD J. MOSSINGHOFF

Attesting Officer

Commissioner of Patents and Trademarks

Disclaimer 4,361,473.—*Chung Chang Young,* Natick, and *John P. Willis,* Sudbury, Mass. POTASSIUM ION-SELECTIVE MEMBRANE ELECTRODE. Patent dated Nov. 30, 1982. Disclaimer filed May 28, 1986, by the assignee, *Nova Biomedical Corp.*

Hereby enters this disclaimer to claims 12–14 of said patent.
[*Official Gazette August 5, 1986.*]